United States Patent
Yabe (10) Patent No.: US 11,744,436 B2
(45) Date of Patent: Sep. 5, 2023

(54) SUBJECT OBSERVATION SYSTEM, LIGHT SOURCE APPARATUS FOR ENDOSCOPE, METHOD OF OPERATING SUBJECT OBSERVATION SYSTEM, AND RECORDING MEDIUM

(71) Applicant: OLYMPUS CORPORATION, Tokyo (JP)

(72) Inventor: Yusuke Yabe, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 644 days.

(21) Appl. No.: 16/930,859

(22) Filed: Jul. 16, 2020

(65) Prior Publication Data
US 2020/0345221 A1 Nov. 5, 2020

Related U.S. Application Data

(63) Continuation of application No. PCT/JP2018/025888, filed on Jul. 9, 2018.

(30) Foreign Application Priority Data

Feb. 28, 2018 (JP) ................................ 2018-035269

(51) Int. Cl.
*A61B 1/00* (2006.01)
*A61B 1/045* (2006.01)
(Continued)

(52) U.S. Cl.
CPC ...... *A61B 1/00006* (2013.01); *A61B 1/00009* (2013.01); *A61B 1/045* (2013.01);
(Continued)

(58) Field of Classification Search
None
See application file for complete search history.

(56) References Cited

U.S. PATENT DOCUMENTS 6,319,198 B1 * 11/2001 Takahashi ............ A61B 1/0655
348/69
6,545,703 B1 * 4/2003 Takahashi .............. H04N 23/74
348/625
(Continued)

FOREIGN PATENT DOCUMENTS

EP        3205258 A1    8/2017
JP    2014-230708 A    12/2014
(Continued)

OTHER PUBLICATIONS

International Search Report dated Sep. 4, 2018 issued in PCT/JP2018/025888.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

A subject observation system includes a light source, a light sensor, an image pickup device, a light source controller configured to cause the light source to alternately perform low-luminance illumination and high-luminance illumination at a predetermined luminance ratio, and a video processor configured to generate an HDR image, and sets a target sensor value S(n) in a temporarily succeeding n frame based on a sensor value S(n−1) in a temporarily preceding (n−1) frame and the luminance ratio.

12 Claims, 6 Drawing Sheets

(51) Int. Cl.
*A61B 1/06* (2006.01)
*H04N 23/74* (2023.01)
*H04N 23/741* (2023.01)
*H04N 23/50* (2023.01)

(52) U.S. Cl.
CPC .......... *A61B 1/0655* (2022.02); *H04N 23/74* (2023.01); *H04N 23/741* (2023.01); *H04N 23/555* (2023.01)

(56) References Cited

U.S. PATENT DOCUMENTS

| | | | | |
|---|---|---|---|---|
| 2010/0309362 | A1* | 12/2010 | Nagata | H04N 23/667 |
| | | | | 348/335 |
| 2013/0321602 | A1* | 12/2013 | Hayama | A61B 1/0655 |
| | | | | 348/68 |
| 2014/0160260 | A1* | 6/2014 | Blanquart | A61B 1/045 |
| | | | | 348/68 |
| 2014/0171737 | A1* | 6/2014 | Kagaya | H04N 25/531 |
| | | | | 600/109 |
| 2016/0183775 | A1* | 6/2016 | Blanquart | G02B 23/2484 |
| | | | | 600/109 |
| 2017/0105258 | A1* | 4/2017 | Sakai | A61B 1/04 |
| 2018/0325365 | A1* | 11/2018 | Fujinuma | G03B 21/204 |
| 2020/0078108 | A1* | 3/2020 | Richmond | A61B 1/00006 |
| 2020/0400830 | A1* | 12/2020 | Talbert | H04N 13/214 |
| 2021/0251502 | A1* | 8/2021 | Oberlin | A61B 5/72 |
| 2021/0378591 | A1* | 12/2021 | Cahill | A61B 5/0071 |
| 2022/0086412 | A1* | 3/2022 | Verma | A61B 1/0655 |
| 2022/0192521 | A1* | 6/2022 | Oberlin | A61B 1/06 |

FOREIGN PATENT DOCUMENTS

| | | |
|---|---|---|
| JP | 2015-073772 A | 4/2015 |
| JP | 2015-530893 A | 10/2015 |
| WO | WO 2014/018951 A1 | 1/2014 |
| WO | WO 2016/056459 A1 | 4/2016 |
| WO | WO 2016/104386 A1 | 6/2016 |

* cited by examiner

SUBJECT OBSERVATION SYSTEM, LIGHT SOURCE APPARATUS FOR ENDOSCOPE, METHOD OF OPERATING SUBJECT OBSERVATION SYSTEM, AND RECORDING MEDIUM

CROSS REFERENCE TO RELATED APPLICATION

This application is a continuation application of PCT/JP2018/025888 filed on Jul. 9, 2018 and claims benefit of Japanese Application No. 2018-035269 filed in Japan on Feb. 28, 2018, the entire contents of which are incorporated herein by this reference.

BACKGROUND OF THE INVENTION

1. Field of the Invention

The present invention relates to a subject observation system that alternately performs low-luminance illumination and high-luminance illumination to generate a high dynamic range image, a light source apparatus for an endoscope, a method of operating the subject observation system, and a recording medium.

2 Description of the Related Art

A technique for acquiring a low-luminance image with a small exposure amount and a high-luminance image with a larger exposure amount than the low-luminance image and synthesizing the low-luminance image and the high-luminance image to generate a high dynamic range (HDR) image having a wider dynamic range than one picked-up image (an HDR technique) has been conventionally proposed.

In a field of application of an endoscope, it is essential that there is no environmental illumination light. Thus, a subject to be observed is irradiated with illumination light when observed. At this time, a close subject appears bright and a far subject appears dark even if irradiated with the same illumination light amount. Thus, halation, underexposure, or the like may occur in an endoscope image.

When the above-described HDR technique is used, halation and underexposure can be respectively suppressed by using a corresponding image portion of a low-luminance image in a halation portion of the high-luminance image and using a corresponding image portion of the high-luminance image in an underexposure portion of the low-luminance image. Therefore, application of the HDR technique to a field of an endoscope has been paid attention to.

When the low-luminance image and the high-luminance image are acquired in the endoscope, an amount of illumination light to be irradiated is made to differ because there is no environmental illumination light, as described above. More specifically, low-luminance illumination is performed when the low-luminance image is acquired, and high-luminance illumination with a larger light amount than low-luminance illumination is performed when the high-luminance image is acquired.

As such a technique, International Publication No. WO2016/104386, for example, describes a light adjusting apparatus that sets an exposure amount for synthesizing a plurality of image data obtained by a plurality of types of exposure processing with different exposure amounts to generate composite image data, the light adjusting apparatus including a brightness detection unit configured to acquire image data or composite image data to detect a brightness of an image, a reference exposure amount calculation unit configured to calculate a reference exposure amount based on a detection result by the brightness detection unit, and an exposure amount setting unit configured to set an exposure amount corresponding to a timing of exposure processing based on the reference exposure amount calculated by the reference exposure amount calculation unit. Further, the publication describes using a white LED (light emitting diode) or a red LED, a green LED, and a blue LED as a light source and performing light adjustment by a combination of current light adjustment and PWM (pulse width modulation) light adjustment, for example.

A light emitting semiconductor device such as an LED tends to decrease in light emission efficiency when a temperature increases to decrease in intensity of light to be emitted even if given the same current value. A temperature of the light emitting semiconductor device increases when a light emission amount is increased (e.g., a distance to a subject is far), and decreases when the light emission amount is decreased (e.g., the distance to the subject is close). Accordingly, the light emission efficiency of the light emitting semiconductor device changes depending on at which distance the subject to be observed exists, for example.

Further, if there are a plurality of light emitting semiconductor devices configured to respectively generate lights in a plurality of colors, the light emitting semiconductor devices differ in temperature dependency of a light emission efficiency depending on which color light the light emitting semiconductor device generates.

SUMMARY OF THE INVENTION

A subject observation system according to an aspect of the present invention includes a light source configured to generate light having an intensity corresponding to a current value of an applied driving current as illumination light, a light sensor configured to detect the intensity of the illumination light to generate a sensor value S, an image pickup device configured to pick up an image of return light from a subject irradiated with the illumination light to generate an image pickup signal sequentially for each frame, a light source controller configured to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame, and a video processor configured to synthesize a high-luminance image pickup signal generated in the high-luminance frame and a low-luminance image pickup signal generated in the low-luminance frame out of the two consecutive high- and low-luminance frames, to generate one high dynamic range image, in which the light source controller sets, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and applies the driving current to the light source in the n frame such that the target sensor value S(n) is generated by the light sensor.

A light source apparatus for an endoscope according to an aspect of the present invention is a light source apparatus for an endoscope connectable to an endoscope system including an image pickup device configured to pick up an image of return light from a subject irradiated with illumination light to generate an image pickup signal sequentially for each frame and a video processor configured to synthesize a high-luminance image pickup signal generated in the high-luminance frame and a low-luminance image pickup signal generated in the low-luminance frame out of two consecutive high- and low-luminance frames, to generate one high dynamic range image, the light source apparatus for an endoscope including a light source configured to generate light having an intensity corresponding to a current value of an applied driving current as the illumination light, a light sensor configured to detect the intensity of the illumination light to generate a sensor value S, and a light source controller configured to apply the driving current to the light source to cause the light source to alternately perform low-luminance illumination in the low-luminance frame and high-luminance illumination in the high-luminance frame and perform control such that an intensity of illumination light in the low-luminance frame has a predetermined luminance ratio to an intensity of illumination light in the high-luminance frame, in which the light source controller sets, when a temporarily preceding frame and a temporarily succeeding frame out of the two consecutive high- and low-luminance frames are respectively an (n−1) frame and an n frame, and a sensor value S generated by the light sensor in the (n−1) frame is S(n−1), a target sensor value S(n) for the n frame using the sensor value S(n−1) and the luminance ratio, and applies the driving current to the light source in the n frame such that the target sensor value S(n) is generated by the light sensor.

A method of operating a subject observation system according to an aspect of the present invention includes causing a light source to emit light having an intensity corresponding to a current value of an applied driving current as illumination light, causing a light sensor to detect the intensity of the illumination light to generate a sensor value S, causing an image pickup device to pick up an image of return light from a subject irradiated with the illumination light to generate an image pickup signal sequentially for each frame, causing a light source controller to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame, causing a video processor to synthesize a high-luminance image pickup signal generated in the high-luminance frame and a low-luminance image pickup signal generated in the low-luminance frame out of the two consecutive high- and low-luminance frames, to generate one high dynamic range image, causing the light source controller to set, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and apply the driving current to the light source in the n frame such that the target sensor value S(n) is generated by the light sensor.

A recording medium according to an aspect of the present invention is a non-transitory computer-readable recording medium storing an operation program for a subject observation system executed by a computer, the operation program causing a subject observation system including a light source configured to generate illumination light, a light sensor configured to detect an intensity of the illumination light, a light source controller configured to apply a driving current to the light source, an image pickup device configured to pick up an image of return light from a subject irradiated with the illumination light, and a video processor configured to generate an image based on an image pickup signal obtained by image pickup by the image pickup device, to cause the light source to generate light having an intensity corresponding to a current value of the applied driving current as the illumination light, cause the light sensor to detect the intensity of the illumination light to generate a sensor value S, cause the image pickup device to pick up an image of return light from a subject irradiated with the illumination light to generate the image pickup signal sequentially for each frame, cause the light source controller to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame, cause the video processor to synthesize a high-luminance image pickup signal generated in the high-luminance frame and a low-luminance image pickup signal generated in the low-luminance frame out of the two consecutive high- and low-luminance frames, to generate one high dynamic range image, and cause the light source controller to set, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and apply the driving current to the light source in the n frame such that the target sensor value S(n) is generated by the light sensor.

DETAILED DESCRIPTION OF THE PREFERRED EMBODIMENTS

Embodiments of the present invention will be described below with reference to the drawings.

First Embodiment

Figure 1:
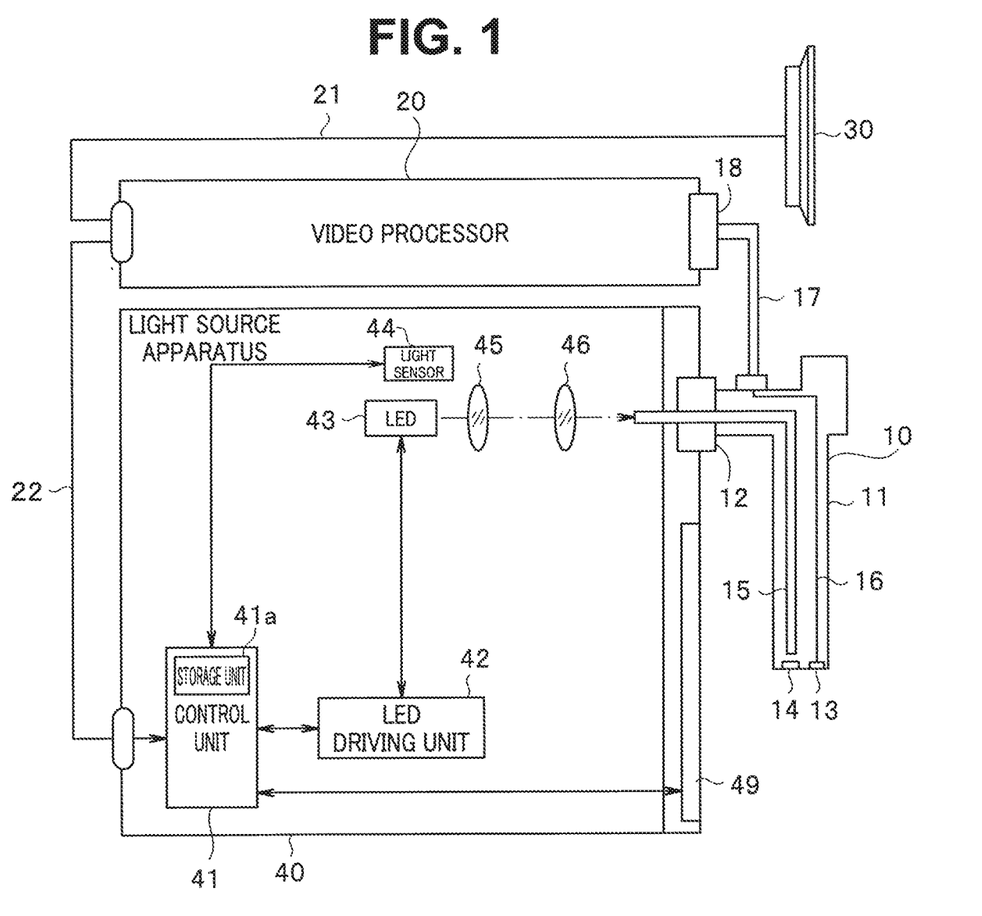
FIG. 1 is a diagram illustrating a configuration of a subject observation system according to a first embodiment of the present invention.

FIGS. 1 to 4 are diagrams each illustrating a first embodiment of the present invention, where FIG. 1 is a diagram illustrating a configuration of a subject observation system.

The present embodiment is an example in which white light observation is performed by using a white LED (light emitting diode), for example, when observation is performed by alternately performing low-luminance illumination and high-luminance illumination for each frame to generate a high dynamic range (HDR) image. However, the present embodiment may be an example in which monochromatic light observation is performed by using a monochromatic LED.

The subject observation system according to the present embodiment is configured as an endoscope system that observes a subject using an endoscope 10.

In other words, the endoscope system includes the endoscope 10, a video processor 20, a monitor 30, and a light source apparatus for endoscope 40 (abbreviated as a light source apparatus 40 in the drawings and hereinafter).

The endoscope 10 includes an elongated insertion section 11, which can be inserted into the subject, on its distal end side. The subject may be an object to be inspected, e.g., an inside of a body cavity in a human body, a living body other than the human body, or an object, other than the living body, such as an engine plant.

An image pickup section 13 including an objective optical system and an image pickup device is provided in a distal end portion of the insertion section 11. The objective optical system forms an image of return light from the subject irradiated with illumination light as an optical image, and is configured to include one or more optical lenses and an optical aperture, for example. The image pickup device picks up the optical image formed by the objective optical system to generate an image pickup signal sequentially for each frame. More specifically, the image pickup device is configured to include a sensor such as a CCD (charge coupled device) or a CMOS (complementary metal oxide semiconductor).

Further, an illumination lens 14 configured to irradiate the subject with illumination light transmitted from the light source apparatus 40 via a light guide 15 is disposed in the distal end portion of the insertion section 11.

In other words, an emission end surface as a distal end surface of the light guide 15 is arranged at a position where the illumination lens 14 is irradiated with illumination light. The light guide 15 is arranged within the insertion section 11 in a longitudinal direction of the insertion section 11, and is further provided to extend into the connector 12 provided on a proximal end side of the endoscope 10.

A signal line 16 is connected to the above-described image pickup section 13. The signal line 16 is arranged within the insertion section 11 in the longitudinal direction of the insertion section 11. A cable 17 is provided to extend from the endoscope 10, and the endoscope 10 is detachably connected to the video processor 20 via a connector 18 provided in a distal end portion of the cable 17. The signal line 16 is provided to extend into the cable 17, and is connected to the connector 18.

By such a configuration, the image pickup section 13 is electrically connected to the video processor 20 via the signal line 16 and the connector 18.

The video processor 20 is an image processing apparatus configured to drive the image pickup section 13 and process the image pickup signal obtained from the image pickup section 13 using a video processing circuit.

In other words, the video processor 20 generates a driving signal including a synchronization signal and supplies the generated driving signal to the image pickup section 13, to drive the image pickup section 13 while controlling an operation. As a result, the image pickup section 13 performs image pickup in units of frames, for example, to generate a movie and output the generated movie as an image pickup signal. Thus, the image pickup signal outputted from the image pickup section 13 is transmitted to the video processor 20.

The video processor 20 performs signal processing for the image pickup signal, to generate an image signal that can be displayed on the monitor 30. The video processor 20 outputs the generated image signal to the monitor 30 via a cable 21 configured to connect the video processor 20 and the monitor 30 to each other. As a result, an endoscope image is displayed on a display screen of the monitor 30.

The subject observation system according to the present embodiment can be set to a normal observation mode for generating an observation image corresponding to one frame from the image pickup signal acquired by image pickup corresponding to one frame and an HDR observation mode for generating an HDR image from an image pickup signal acquired under low-luminance illumination and an image pickup signal acquired under high-luminance illumination. Description of the normal observation mode is omitted, and the HDR observation mode will be described.

When the subject observation system is set to the HDR observation mode, the light source apparatus 40 alternately performs low-luminance illumination and high-luminance illumination for each frame.

In this case, the video processor 20 functions as an image generation section configured to synthesize a high-luminance image pickup signal generated in a high-luminance frame and a low-luminance image pickup signal generated in a low-luminance frame out of two consecutive high- and low-luminance frames to generate one high-dynamic range image. Therefore, the present embodiment adopts a so-called time-division HDR method.

The video processor 20 detects a brightness of an image based on the image pickup signal obtained from the image pickup section 13. The video processor 20 generates a light source control signal for controlling the light source apparatus 40 such that the detected brightness of the image is a target brightness.

An example of the light source control signal is information about a ratio of a target brightness of a high-luminance image in a current frame to be subsequently acquired to a brightness of a high-luminance image in a latest frame already acquired (the present invention is not limited to this, but the light source control signal may be information about a difference, for example, instead of the information about the ratio, or may be generated based on a low-luminance image instead of the high-luminance image).

The light source control signal is outputted from the video processor 20, and is transmitted to the light source apparatus 40 via a communication cable 22 configured to connect the video processor 20 and the light source apparatus 40 to each other.

The light source apparatus 40 includes a control unit 41, an LED driving unit 42, an LED 43, a light sensor 44, a lens 45, a lens 46, and an operation panel 49.

The control unit 41 is connected to the LED driving unit 42, the light sensor 44, and the operation panel 49. The light source control signal from the video processor 20 is inputted to the control unit 41. The control unit 41 outputs light adjustment information to the LED driving unit 42 based on an operation input from the operation panel 49, a sensor value S generated by the light sensor 44, and the light source control signal from the video processor 20 to control an inside of the light source apparatus 40.

A nonvolatile storage unit 41a (memory) is provided inside, for example, the control unit 41 (the storage unit 41a may be provided outside the control unit 41). The storage unit 41a stores information about a luminance ratio RI(L/H) as an internal set value. The LED driving unit 42 applies a pulse-shaped driving current to the LED 43, as described below. The storage unit 41a in the present embodiment further stores information about a duty/duty ratio (hereinafter referred to as DD ratio) RD(L/H) as an internal set value.

When a high-luminance sensor value generated by the light sensor 44 in the high-luminance frame and a low-luminance sensor value generated by the light sensor 44 in the low-luminance frame in the pair of high- and low-luminance frames in which the high-luminance image and the low-luminance image for constituting the HDR image are respectively acquired are respectively represented by SH and SL, the luminance ratio RI(L/H) is a ratio of the low-luminance sensor value SL to the high-luminance sensor value SH, as expressed by the following equation:

$$RI(L/H)=SL/SH$$

The luminance ratio RI(L/H) is a fixed value more than 0 and less than 1, which does not change even when a brightness of an image is changed.

The DD ratio RD(L/H) is a ratio of a duty ratio DL of the pulse-shaped driving current to be applied to the LED 43 in the low-luminance frame to a duty ratio DH of the pulse-shaped driving current to be applied to the LED 43 in the high-luminance frame, as expressed by the following equation:

$$RD(L/H)=DL/DH.$$

The DD ratio RD(L/H) is a fixed value more than 0 and equal to or less than 1, which does not change even when a brightness of an image is changed. Therefore, storage and acquisition of the DD ratio RD(L/H) may be omitted, assuming that RD(L/H)=1, for example (see a second embodiment, described below).

Although the luminance ratio RI(L/H) and the DD ratio RD(L/H) are each a ratio of a value in the low-luminance frame to a value in the high-luminance frame, the ratio may be replaced with a ratio of the value in the high-luminance frame to the value in the low-luminance frame. In this case, although the luminance ratio RI(H/L) and the DD ratio RD(H/L) may be used, the luminance ratios are respectively reciprocals of the luminance ratio RI(L/H) and the DD ratio RD(L/H). Thus, whichever of the luminance ratio RI(L/H) and the DD ratio RD(L/H), and the luminance ration RI(H/L) and the DD ratio RD(H/L) are stored in the storage unit 41a, a substantially identical function and effect can be obtained.

A light amount of illumination light in one frame is proportional to a product of a sensor value S and a duty ratio D, and is expressed by the following equations:

light emission amount in high-luminance frame=$k \times SH \times DH$, and light emission amount in low-luminance frame=$k \times SL \times DL$, where k is a proportionality constant.

Therefore, a light amount ratio r(L/H) as a ratio of the light amount of illumination light in the low-luminance frame to the light amount of illumination light in the high-luminance frame is expressed by the following equation:

$$r(L/H)=SL \times DL/(SH \times DH).$$

Since a right side of the foregoing equation is a value obtained by multiplying the luminance ratio RI(L/H) and the DD ratio RD(L/H), the light amount ratio r(L/H) can also be written as:

$$r(L/H)=RI(L/H) \times RD(L/H).$$

Therefore, the light amount ratio r(L/H) is a value more than 0 and less than 1.

The control unit 41 outputs a current value and a pulse width of the driving current to be applied as a pulse to the LED 43 as a light emitting semiconductor device as light adjustment information to the LED driving unit 42.

At this time, control of a light emission amount (light adjustment) of the LED 43 by the LED driving unit 42 is basically performed by pulse width light adjustment for applying a current in a shape of a pulse within one frame to control a pulse width of the pulse to be applied (by so-called PWM (pulse width modulation)). Note that a duty ratio, for example, is used as a unit representing a pulse width. On the other hand, although control of a light emission intensity by controlling the current value of the driving current is used only for a change in a light emission efficiency of the LED 43 due to a temperature change or the like, details of the control will be described below.

The LED driving unit 42 causes the LED 43 to emit light by generating a pulse-shaped driving current a current value and a pulse width of which have been set based on the light adjustment information from the control unit 41 and applying the generated driving current to the LED 43.

The control unit 41 and the LED driving unit 42 are each a light source control unit (light source controller) configured to apply the driving current to the LED 43 to cause the LED 43 to alternately perform low-luminance illumination in the low-luminance frame and high-luminance illumination in the high-luminance frame.

Thus, the LED 43 emits light only for a light emission period corresponding to a duty ratio of a PWM pulse at a light emission intensity corresponding to a current value of the driving current to be applied from the LED driving unit 42 in an image pickup period corresponding to one frame.

The LED 43 is a light source unit (light source) configured to generate as illumination light having an intensity corresponding to the current value of the driving current to be applied. Note that although an LED is taken as an example of the light emitting semiconductor device (light emitting element) in the present embodiment, the present invention is not limited to this. For example, a light emitting semiconductor device such a laser diode (LD) may be used.

The LED 43 in the present embodiment is configured as a white LED configured to emit white light, for example, as described above. When the current value of the driving current to be applied to the LED 43 is represented by I, an intensity of illumination light to be emitted by the LED 43 within a range (Imin≤I≤Imax) of a rated current from a minimum current value Imin to a maximum current value Imax is a monotonically increasing function of the current value I.

The light sensor 44 detects the intensity of the illumination light to be emitted from the LED 43, to generate the sensor value S. If the sensor value S is a monotonically increasing function of the intensity of the illumination light (e.g., if the sensor value S is proportional to the intensity of the illumination light), the sensor value S generated by the light sensor 44 is a monotonically increasing function of the current value I (similarly, the current value I is also a monotonically increasing function of the sensor value S). Therefore, to acquire a desired sensor value S, the current value I of the driving current to be applied to the LED 43 may be controlled (more specifically, the current value I may be increased if the sensor value S is desired to be increased, and may be decreased if the sensor value S is desired to be decreased).

Note that the light sensor 44 in the present embodiment assumes a non-integral type for converting received light into an electrical signal in real time (i.e., a type different from an integral type for integrating a light emission intensity within one frame over time to detect a light emission amount in one frame). Therefore, when pulse width control is performed, the sensor value S other than zero is outputted at the time of light emission. However, the sensor value S becomes zero at the time of non-light emission. Accordingly, it is assumed that the sensor value S described in the present embodiment is a sensor value at the time of light emission.

The lens 45 is arranged on an optical path of emitted light from the LED 43, and converts the light emitted from the LED 43 into substantially parallel light and emits the substantially parallel light.

The lens 46 is arranged on an optical axis of the lens 45, and irradiates light from the lens 45 as parallel light onto an incidence end surface of the light guide 15.

The operation panel 49 is an operation section including a touch panel and an operation switch, for example, and configured to perform setting for the light source apparatus 40 when operated by a user. A signal generated by operating the operation panel 49 is inputted to the control unit 41. A current set value of the light source apparatus 40, for example, can be displayed on the operation panel 49.

Figure 2:
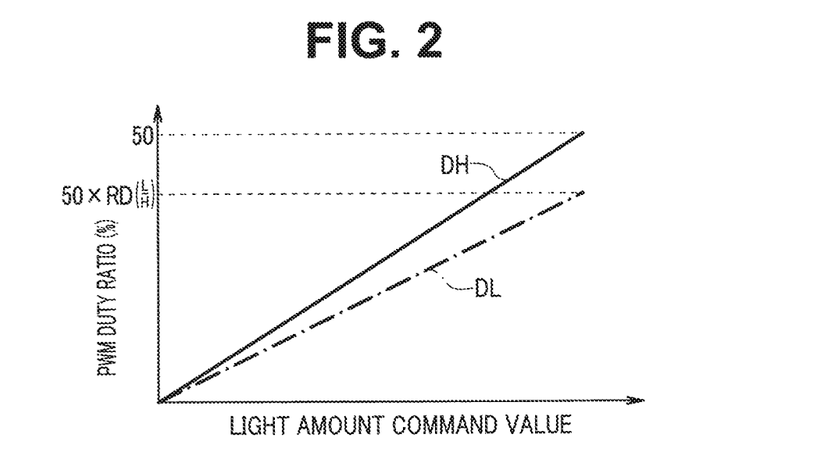
FIG. 2 is a diagram illustrating how high-luminance illumination and low-luminance illumination are subjected to PWM control based on a light source control signal in the first embodiment.

FIG. 2 is a diagram illustrating how high-luminance illumination and low-luminance illumination are subjected to PWM control based on a light source control signal.

As described above, control of a light emission amount of the LED 43 by the LED driving unit 42 is basically performed by pulse width light adjustment for changing a duty ratio. In other words, both a duty ratio DH of a current to be applied to the LED 43 at the time of high-luminance illumination and a duty ratio DL of a current to be applied to the LED 43 at the time of low-luminance illumination are increased or decreased in proportion to a light amount command value. The light amount command value is a target value of a light amount in a high-luminance frame, which is represented by the light source control signal.

The control unit 41 controls the LED driving unit 42 such that the DD ratio RD(L/H) stored in the storage unit 41a is realized even if the light amount command value is any value. As a result, a ratio between the duty ratio DH and the duty ratio DL is always maintained as a DD ratio RD(L/H). The DD ratio RD(L/H) is a value more than 0 and equal to or less than 1.

Thus, the control unit 41 and the LED driving unit 42 as a light source control unit adjust a first pulse width of the a driving current to be applied to the LED 43 in the high-luminance frame based on the light source control signal, and performs control such that a second pulse width of the driving current to be applied to the LED 43 in a low-luminance frame has a predetermined DD ratio RD(L/H) to the first pulse width.

Figure 3:
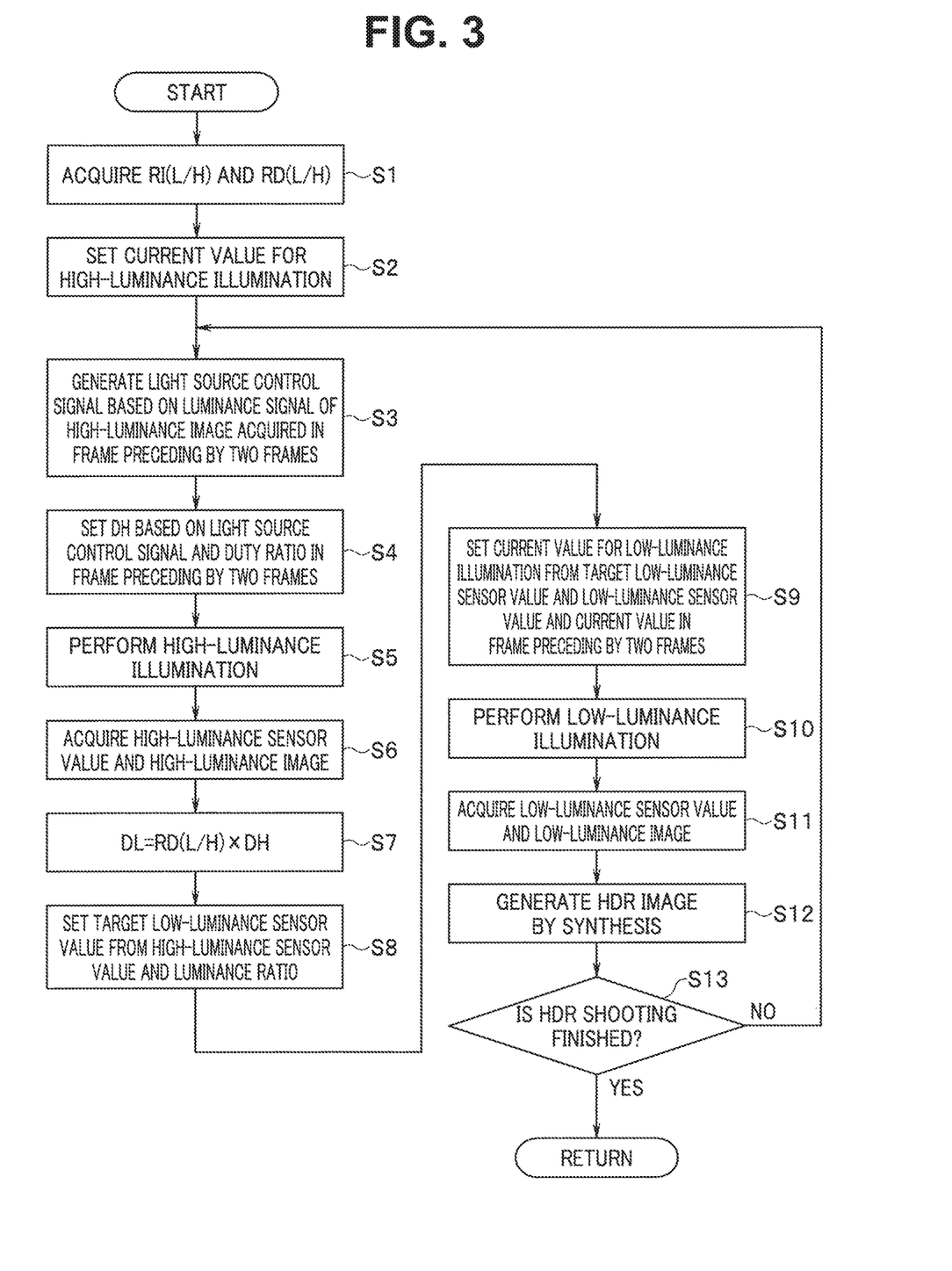
FIG. 3 is a flowchart illustrating a function of the subject observation system according to the first embodiment.
Figure 4:
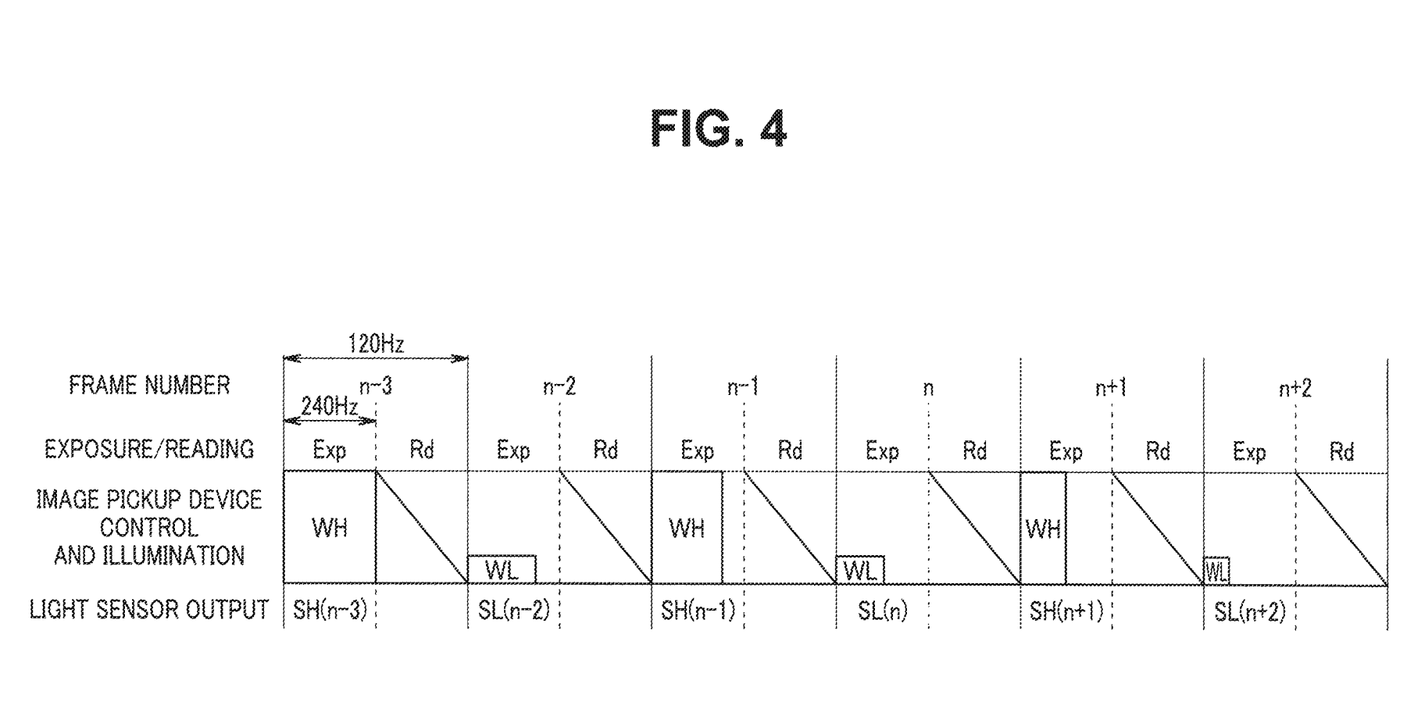
FIG. 4 is a timing chart illustrating an example of light adjustment in the subject observation system according to the first embodiment.

FIG. 3 is a flowchart illustrating a function of the subject observation system, and FIG. 4 is a timing chart illustrating an example of light adjustment in the subject observation system.

Note that FIG. 4 takes as an example a case where a frame period of one frame is $1/120$ seconds (a corresponding frequency is 120 Hz) and one frame period is divided into two periods, i.e., an exposure period Exp of $1/240$ seconds (a corresponding frequency is 240 Hz) and a reading period Rd of $1/240$ seconds (a frequency of 240 Hz). Accordingly, in FIG. 2, a maximum value of the duty ratio DH is set to 50(%). However, a half of one frame period is not limited to the exposure period Exp, and the maximum value of the duty ratio DH is not limited to 50(%).

In the present embodiment, an example in which out of a high-luminance image and a low-luminance image for constituting an HDR image, the high-luminance image is acquired before the low-luminance image, to control the low-luminance frame using the high-luminance frame as a reference is mainly described. On the other hand, the high-luminance image may be acquired after the low-luminance image, to control the high-luminance frame using the low-luminance frame as a reference.

When processing illustrated in FIG. 3 is started, the control unit 41 acquires a luminance ratio RI(L/H) and a DD ratio RD(L/H) from the storage unit 41a (step S1).

Then, the control unit 41 sets a current value IH of a driving current to be applied to the LED 43 at the time of high-luminance illumination (step S2). In the present embodiment, the current value IH is set to a maximum current value Imax in a range of a rated current, for example (note that the present invention is not limited to this, as illustrated in a second embodiment, described below). The control unit 41 performs control such that the current value IH of the driving current to be applied to the LED 43 becomes constant in a high-luminance frame. As a result, the set current value IH=Imax at the time of high-luminance illumination is maintained until HDR shooting is finished.

Note that in the following description, an n-th frame following an image pickup order is referred to as an "n frame". Amounts each varying for each frame, e.g., a brightness B of an image, a duty ratio D, a sensor value S, and a current value IL at the time of low-luminance illumination are respectively assigned frame numbers when described, as needed. It is assumed that a high-luminance image in an (n−1) frame is to be subsequently acquired.

Consequently, the video processor 20 finds a brightness B(n−3) based on a luminance signal of a high-luminance image acquired in a frame preceding the (n−1) frame by two frames, and generates a light source control signal such that the light source control signal includes a brightness ratio RB(n−1) of a target brightness B(n−1) at the time of high-luminance illumination in the (n−1) frame next acquired to the brightness B(n−3), as expressed by the following equation (step S3):

$$RB(n-1)=B(n-1)/B(n-3).$$

The video processor 20 transmits the generated light source control signal to the control unit 41.

The control unit 41 sets a duty ratio DH(n−1) corresponding to the (n−1) frame, as expressed by the following equation, based on the brightness ratio RB(n−1) included in the light source control signal and a duty ratio DH(n−3) in a high-luminance frame preceding the (n−1) frame by two frames (step S4):

$$DH(n-1)=RB(n-1) \times DH(n-3).$$

The current value IH of the driving current in the high-luminance frame is fixed at the maximum current value Imax, as described above, and the duty ratio DH(n−1) is set in step S4. Thus, the control unit 41 controls the LED driving unit 42 based on the setting, to cause the LED 43 to perform high-luminance illumination in the (n−1) frame (step S5).

While the LED 43 is emitting light, the light sensor 44 detects an intensity of light, to generate and output a high-luminance sensor value SH(n−1) at the time of high-luminance illumination. Note that even if the current value is fixed to the maximum current value Imax, the light emission efficiency of the LED 43 may change depending on the temperature change or the like, as described above. Thus, the high-luminance sensor value SH may change. When an exposure period Exp in the (n−1) frame is finished, a reading period Rd starts. In the reading period Rd, an image pickup signal is read out. The video processor 20 generates a high-luminance image based on the read image pickup signal (step S6).

The succeeding n frame is a frame in which a low-luminance image paired with the high-luminance image is generated to generate an HDR image.

The control unit 41 multiplies the duty ratio DH(n−1) in the (n−1) frame by the DD ratio RD(L/H) read out in step S1, to calculate a duty ratio DL(n) in the n frame as a low-luminance frame, as expressed by the following equation (step S7):

$$DL(n)=RD(L/H) \times DH(n-1).$$

If the duty ratio DH in the high-luminance frame and the duty ratio DL in the low-luminance frame are made the same, assuming that the DD ratio RD(L/H)=1, as described above (see a second embodiment, described below), a process in step S7 may be omitted.

Further, the control unit 41 calculates a target low-luminance sensor value SL(n), as expressed by the following equation, based on the high-luminance sensor value SH(n−1) acquired in the (n−1) frame and the luminance ratio RI(L/H) read out in step S1 (step S8):

$$SL(n)=SH(n-1) \times RI(L/H).$$

If the low-luminance frame is used as a reference instead of the high-luminance frame being used as a reference, a target high-luminance sensor value SH(n), as expressed by the following equation, may be calculated based on a low-luminance sensor value SL(n−1) acquired in the (n−1) frame and the luminance ratio RI(L/H) read out in step S1:

$$SH(n)=SL(n-1)/RI(L/H).$$

Further, the control unit 41 calculates a current value IL(n) of the driving current to be applied to the LED 43 in the n frame, as expressed by the following equation, based on the target low-luminance sensor value SL(n), a low-luminance sensor value SL(n−2) in a low-luminance frame preceding the n frame by two frames, and a current value IL(n−2) in the low-luminance frame preceding the n frame by two frames (step S9):

$$IL(n)=\{IL(n-2) \times SL(n)/SL(n-2)\}.$$

Accordingly, a method of calculating, based on a driving current value in a just preceding frame that is the same in type of low-luminance/high-luminance as a frame, a subsequent driving current value is adopted because the change in the light emission efficiency of the LED 43 due to the temperature change or the like may be considered to be small in a frame preceding the frame by two frames.

If the low-luminance frame is used as a reference, a current value IH(n) of the driving current to be applied to the LED 43 in the n frame, as expressed by the following equation, may be calculated based on the target high-luminance sensor value SH(n), a high-luminance sensor value SH(n−2) in a high-luminance frame preceding the n frame by two frames, and a current value IH(n−2) in the high-luminance frame preceding the n frame by two frames:

$$IH(n)=\{IH(n-2) \times SH(n)/SH(n-2)\}.$$

The control unit 41 sets the current value IL(n) and the duty ratio DL(n) thus calculated in the LED driving unit 42. The LED driving unit 42 applies a pulse-shaped driving current based on set values to the LED 43, to perform low-luminance illumination in the n frame (step S10).

Thus, the control unit 41 and the LED driving unit 42 as a light source control unit set a target sensor value S(n) for the n frame, and apply the driving current to the LED 43 in the n frame such that the target sensor value S(n) is generated by the light sensor 44.

While the LED 43 is emitting light, the light sensor 44 detects an intensity of light, and generates and outputs the sensor value SL(n) at the time of low-luminance illumination. When an exposure period Exp in the n frame is finished, a reading period Rd starts. In the reading period Rd, an image pickup signal is read out. The video processor 20 generates a low-luminance image based on the read image pickup signal (step S11).

The video processor 20 synthesizes the high-luminance image in the (n−1) frame and the low-luminance image in the n frame, to generate an HDR image (step S12). The generated HDR image is outputted from the video processor 20 to the monitor 30, for example, and an HDR endoscope image is displayed on the display screen of the monitor 30.

Then, it is judged whether or not HDR shooting is finished (step S13). If it is judged that the HDR shooting is not finished, the processing returns to step S3 to acquire a subsequent HDR image. In step S3 and subsequent steps, the above-described processing is performed. If it is judged that the HDR shooting is finished, the processing returns to main processing or the like not illustrated.

Note that instead of the current value IH being kept constant using high-luminance illumination as a reference and the current value IL in low-luminance illumination being changed to match the change in the light emission efficiency of the LED 43, as described above, the current value IL may be kept constant using low-luminance illumination as a reference and the current value IL in high-luminance illumination may be changed.

Instead of light adjustment control being performed using the luminance signal of the high-luminance image to be outputted from the video processor 20 as a reference, light adjustment control may be performed using a luminance signal of a low-luminance image as a reference in such a manner as to output the luminance signal of the low-luminance image from the video processor 20.

Further, instead of control being performed using the duty ratio DH at the time of high-luminance illumination as a reference, control may be performed using the duty ratio DL at the time of low-luminance illumination as a reference.

According to the first embodiment, control is performed such that the current value IH of the driving current to be applied to the LED 43 in the high-luminance frame is constant to basically perform light adjustment by pulse width control. Thus, the first embodiment has an advantage that response becomes faster than when light adjustment is performed by current control. In other words, when the brightness of the image is controlled by current light adjustment, a current value is changed over a plurality of frames, and is adjusted such that a target brightness is obtained by feedback from a brightness of an acquired image so that response is slow. However, according to the present embodiment, PWM light adjustment is adopted so that high responsiveness can be implemented.

The target sensor value S(n) is set based on a sensor value S(n−1) actually measured in the (n−1) frame preceding the n frame by one frame and the previously determined luminance ratio RI(L/H). Thus, a highly accurate HDR image can be obtained by synthesizing the high-luminance image and the low-luminance image while maintaining a brightness ratio between the images with high accuracy.

The current value I(n) of the driving current to be applied to the LED 43 in the n frame that is not a frame used as a reference is a value {(n−2)×S(n)/S(n−2)} based on the target sensor value S(n), a sensor value S(n−2) in the frame preceding the n frame by two frames, and a current value I(n−2) in the frame preceding the n frame by two frames. Thus, a light emission amount at the target sensor value S(n) can be accurately obtained without being virtually affected by the change in the light emission efficiency of the LED 43 due to the temperature change or the like. Thus, the brightness ratio between the high-luminance image and the low-luminance image can be maintained with higher accuracy.

Further, the second pulse width of the driving current in the low-luminance frame has a predetermined DD ratio RD(L/H) to the first pulse width of the driving current in the high-luminance frame. Thus, the DD ratio RD(L/H) can be set to a value less than 1, as needed. Accordingly, respective dynamic ranges of the high-luminance image and the low-luminance image can be made wider. Even when a light source has deteriorated, a light amount ratio between low-luminance illumination and high-luminance illumination can be maintained with high accuracy.

Even if the current value IH to be applied to the LED 43 is maintained at a predetermined value at the time of high-luminance illumination, when the light emission efficiency of the LED 43 changes, the intensity of light in the high-luminance frame (i.e., the high-luminance sensor value SH) also changes depending on the change in the light emission efficiency. However, the current value IL to be applied to the LED 43 at the time of low-luminance illumination is finely adjusted, to cope with the change in the intensity corresponding to the change in the light emission efficiency. Accordingly, a light amount ratio r(L/H) between the high-luminance frame and the low-luminance frame can be kept constant, and a brightness balance between the high-luminance image and the low-luminance image can be kept with high accuracy.

Second Embodiment

Figure 5:
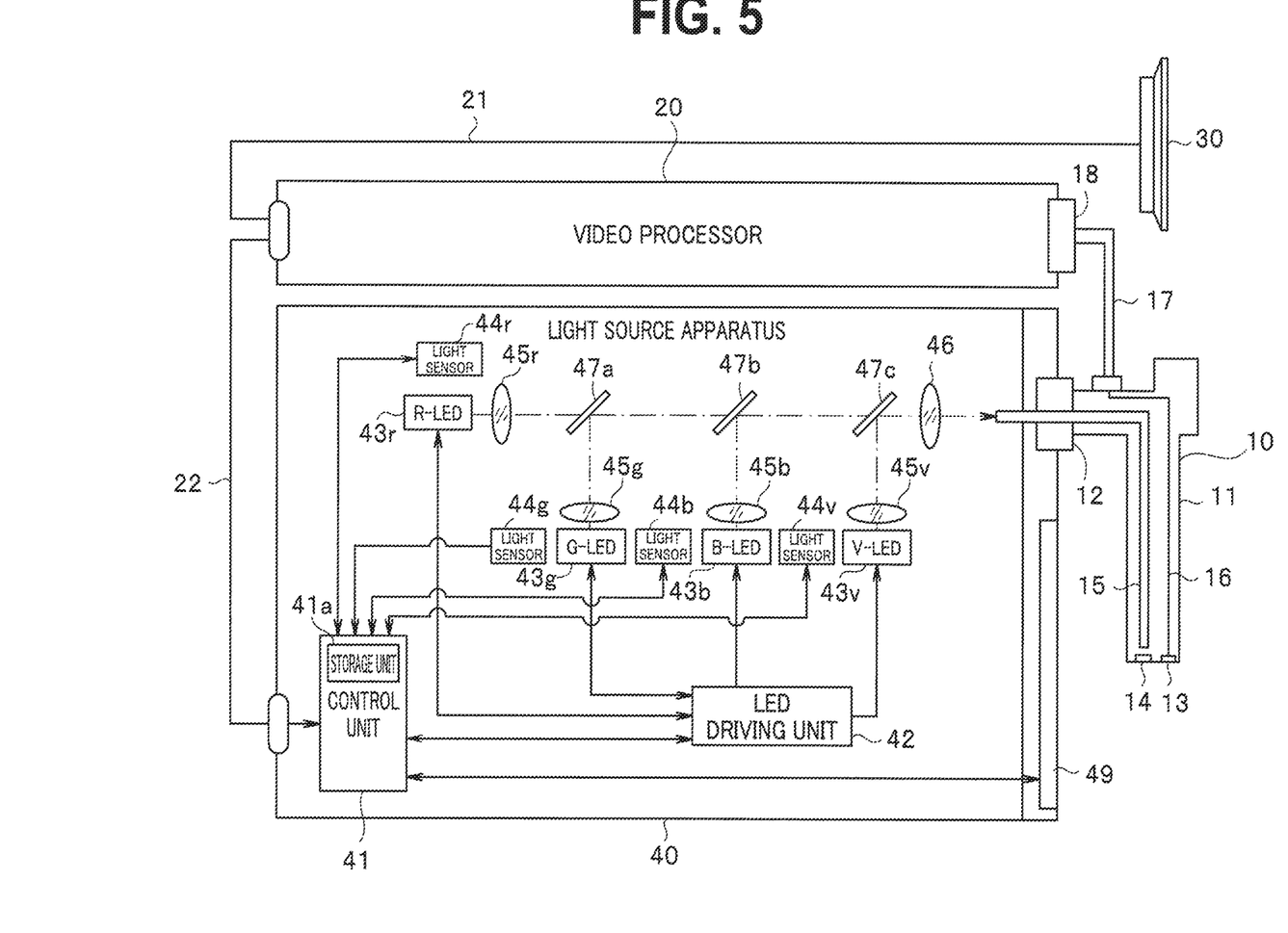
FIG. 5 is a diagram illustrating a configuration of a subject observation system according to a second embodiment of the present invention.
Figure 6:
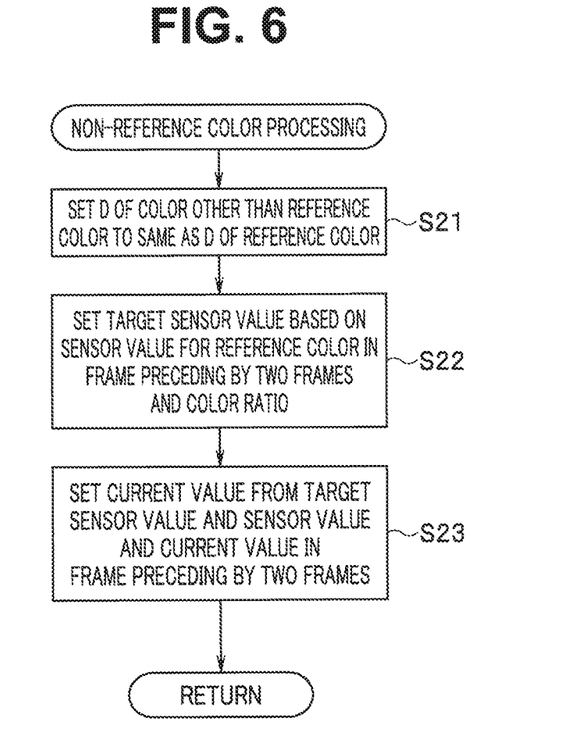
FIG. 6 is a flowchart illustrating non-reference color processing in the subject observation system according to the second embodiment.
Figure 7:
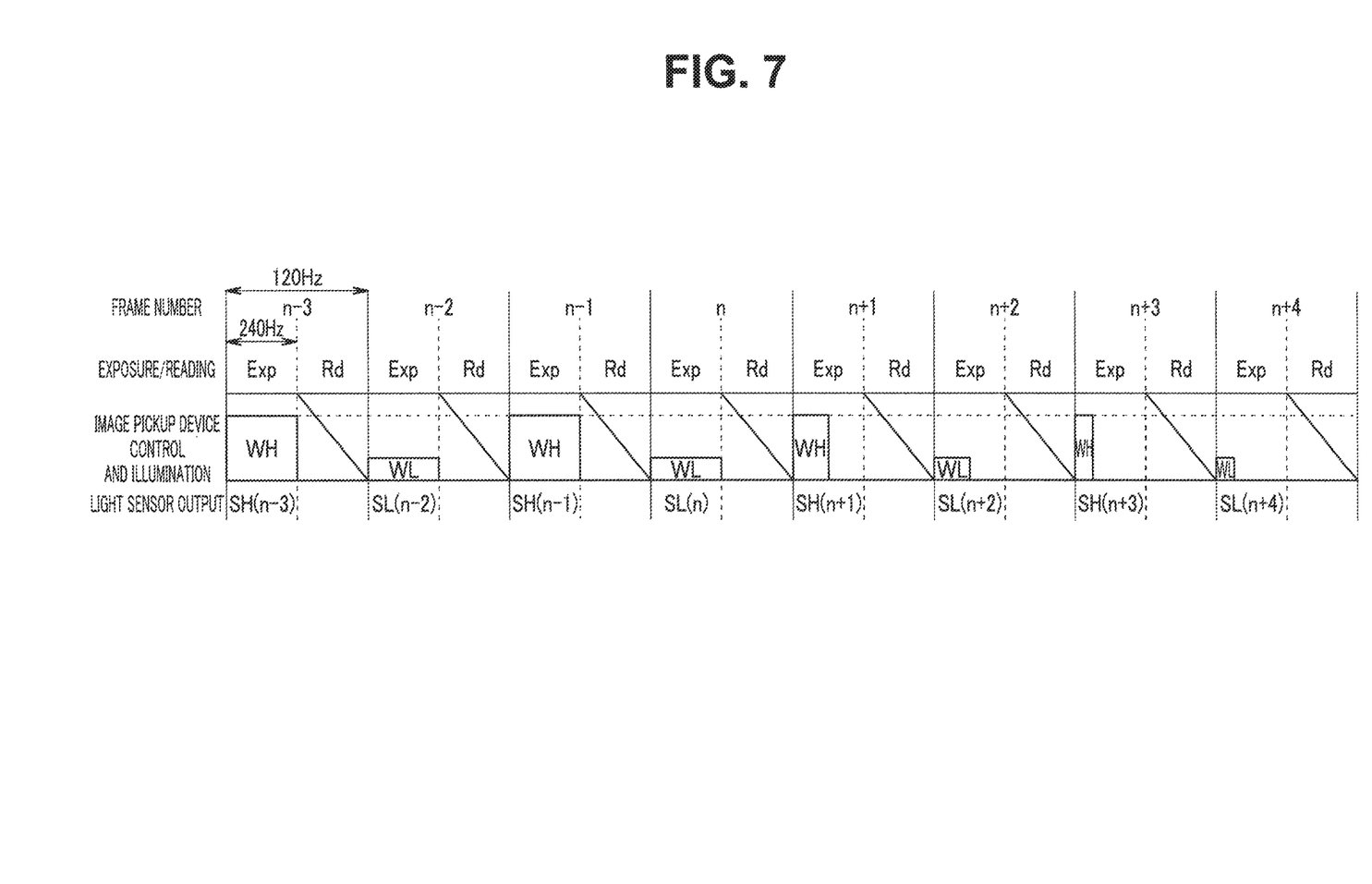
FIG. 7 is a timing chart illustrating an example of light adjustment of a reference color in the subject observation system according to the second embodiment.

FIGS. 5 to 7 are diagrams each illustrating a second embodiment of the present invention, where FIG. 5 is a diagram illustrating a configuration of a subject observation system.

In the second embodiment, description of similar sections to the sections in the above-described first embodiment is appropriately omitted by respectively assigning the sections the same reference numerals, and only differences will be mainly described.

Although the above-described first embodiment is an example of a subject observation system that performs illumination using a white LED (or a monochromatic LED), the present embodiment provides a subject observation system that performs illumination using a plurality of LEDs respectively configured to emit lights in a plurality of colors.

In a light source apparatus 40 in the present embodiment illustrated in FIG. 5, the LED 43, the light sensor 44, and the lens 45 are deleted and an R-LED 43r (R: red), a G-LED 43g (G: green), a B-LED 43b (B: blue), a V-LED 43v (V: violet), light sensors 44r, 44g, 44b, and 44v, lenses 45r, 45g, 45b, and 45v, and dichroic filters 47a, 47b, and 47c are added from and to the light source apparatus 40 in the first embodiment illustrated in FIG. 1.

The R-LED 43r receives a driving current having a current value Ir and a duty ratio Dr from an LED driving unit 42, and emits red light (R light) for only a light emission period corresponding to the duty ratio Dr at a light emission intensity corresponding to the current value Ir.

The G-LED 43g receives a driving current having a current value Ig and a duty ratio Dg from the LED driving unit 42, and emits green light (G light) for only a light emission period corresponding to the duty ratio Dg at a light emission intensity corresponding to the current value Ig.

The B-LED 43b receives a driving current having a current value Ib and a duty ratio Db from the LED driving unit 42, and emits blue light (B light) for only a light emission period corresponding to the duty ratio Db at a light emission intensity corresponding to the current value Ib.

The V-LED 43v receives a driving current having a current value Iv and a duty ratio Dv from the LED driving unit 42, and emits violet light (V light) for only a light emission period corresponding to the duty ratio Dv at a light emission intensity corresponding to the current value Iv.

The R-LED 43r, the G-LED 43g, the B-LED 43b, and the V-LED 43v are each a light source unit (light source).

The control unit 41 in the present embodiment uses one color as a reference color (first color C1), to control a light amount of light in a non-reference color (second color C2) other than the reference color based on the reference color. More specifically, in the present embodiment, an example in which G is a reference color and R, B, and V are each a non-reference color will be described. Note that G is not necessarily a reference color, but light in a color other than G may be used as a reference.

The G-LED 43g is a first light emitting semiconductor device configured to generate light in the first color C1. The R-LED 43r, the B-LED 43b, and the V-LED 43v are each a second light emitting semiconductor device configured to generate light in the second color C2 different from the first color C1.

The light sensors 44r, 44g, 44b, and 44v respectively detect intensities of lights emitted by the R-LED 43r, the G-LED 43g, the B-LED 43b, and the V-LED 43v, and respectively generate and output sensor values SR, SG, SB, and SV.

The light sensor 44g is a first light sensor configured to detect an intensity of light in the first color C1 (here, G) and generate a sensor value SC (here, the sensor value SG). The light sensors 44r, 44b, and 44v are each a second light sensor configured to detect an intensity of light in the second color C2 (here, R, B, V) and generate a sensor value SC2 (here, the sensor values SR, SB, SV).

The sensor values SR, SG, SB, and SV respectively outputted from the light sensors 44r, 44g, 44b, and 44v are inputted to the control unit 41.

The lenses 45*r*, 45*g*, 45*b*, and 45*v* are respectively arranged on optical paths of emitted lights from the R-LED 43*r*, the G-LED 43*g*, the B-LED 43*b*, and the V-LED 43*v*, and respectively convert the lights emitted from the LEDs into substantially parallel lights and emit the substantially parallel lights.

The dichroic filter 47*a* is arranged at a position where an optical axis of the lens 45*r* and an optical axis of the lens 45*g* cross each other. The dichroic filter 47*a* transmits the R light from the R-LED 43*r*, and reflects the G light from the G-LED 43*g*. Thus, the dichroic filter 47*a* synthesizes the R light and the G light.

The dichroic filter 47*b* is arranged at a position where the optical axis of the lens 45*r* and an optical axis of the lens 45*b* cross each other. The dichroic filter 47*a* transmits the R light from the R-LED 43*r* and the G light from the G-LED 43*g*, and reflects the B light from the B-LED 43*b*. Thus, the dichroic filter 47*b* synthesizes the R light, the G light, and the B light.

The dichroic filter 47*c* is arranged at a position where the optical axis of the lens 45*r* and an optical axis of the lens 45*v* cross each other. The dichroic filter 47*b* transmits the R light from the R-LED 43*r*, the G light from the G-LED 43*g*, and the B light from the B-LED 43*b*, and reflects the V light from the V-LED 43*v*. Thus, the dichroic filter 47*b* synthesizes the R light, the G light, the B light, and the V light into white light.

In other words, in the present embodiment, the R light, the G light, the B light, and the V light are synthesized to generate white light (note that the R light, the G light, and the B light may be synthesized to generate white light).

Note that although description is made assuming a case where white light illumination is performed using a simultaneous method in the present embodiment, white light illumination may be performed using a frame sequential method.

A luminance ratio RI(L/H) to be stored in the storage unit 41*a* is a luminance ratio relating to G as a reference color in the present embodiment. Further, the storage unit 41*a* in the present embodiment stores as an internal set value information about a color ratio RC(C2/C1) representing a light amount of light in the second color C2 to a light amount of light in the first color C1. More specifically, the storage unit 41*a* stores information about color ratios RC(R/G), RC(B/G), and RC(V/G).

The color ratio RC(R/G), RC(B/G), and RC(V/G) respectively represent ratios of light intensities of the lights (R light, B light, and V light) in the second color C2 as a non-reference color to an intensity of the light (G light) in the first color C1 as a reference color.

As described above, the intensities of the lights are respectively detected by the light sensors 44*r*, 44*g*, 44*b*, and 44*v*. Therefore, more specifically, the color ratio RC(R/G) is a ratio SR/SG of the sensor value SR to the sensor value SG, the color ratio RC(B/IG) is a ratio SB/SG of the sensor value SB to the sensor value SG, and the color ratio RC(V/G) is a ratio SV/SG of the sensor value SV to the sensor value SG.

The color ratios RC(R/G), RC(B/G), and RC(V/G) are each a fixed value that does not change even when a brightness of an image is changed to keep a white balance.

Note that when a color other than G is set as a reference color, a color ratio to be stored in the storage unit 41*a* is information about a ratio of an intensity of light to the set reference color.

In the present embodiment, the DD ratio RD(L/H) is set to 1 (see FIG. 7). Therefore, the storage of the DD ratio RD(L/H) in the storage unit 41*a* may be omitted. Needless to say, in the configuration of the present embodiment, the DD ratio RD(L/H) may also be set to a value less than 1, like in the above-described first embodiment.

Then, FIG. 6 is a flowchart illustrating non-reference color processing in the subject observation system, and FIG. 7 is a timing chart illustrating an example of light adjustment of a reference color in the subject observation system.

As illustrated in FIG. 7, light adjustment control of G as a reference color is substantially the same as light adjustment control of white light (or monochromatic light) in the above-described first embodiment.

In other words, the control unit 41 and the LED driving unit 42 as a light source control unit perform similar control to the control in the above-described first embodiment for the current value Ig of the driving current to be applied to the G-LED 43*g* based on the sensor value SG. The light source control unit adjusts a first pulse width of the driving current to be applied to the G-LED 43*g* in a high-luminance frame based on a light source control signal and performs control such that a second pulse width of the driving current to be applied to the G-LED 43*g* in a low-luminance frame has a predetermined ratio (DD ratio RD(L/H)) to the first pulse width.

However, the present embodiment differs from the above-described first embodiment in that the current value Ig of the driving current to be applied to the G-LED 43*g* in the high-luminance frame is a predetermined current value less than a maximum current value Imax.

Further, the present embodiment differs from the above-described first embodiment in that the DD ratio RD(H) is set to 1. Thus, the control unit 41 and the LED driving unit 42 as a light source control unit further perform control such that the second pulse width of the driving current to be applied to the G-LED 43*g* in the low-luminance frame is the same as the first pulse width of the driving current to be applied to the G-LED 43*g* in the high-luminance frame.

On the other hand, processing as illustrated in FIG. 6 is performed for a non-reference color.

When the processing illustrated in FIG. 6 is started, the control unit 41 sets a duty ratio D of a non-reference color to the same as a duty ratio D of a reference color (step S21).

More specifically, the respective duty ratios Dr, Db, and Dv of the non-reference colors R, B, and V in the high-luminance frame are each set to the same as the duty ratio Dg of the reference color G in the same high-luminance frame. Therefore, the respective pulse widths of the driving currents to be applied to the R-LED 43*r*, B-LED 43*b*, and V-LED 43*v* in the high-luminance frame are each set to the first pulse width of the driving current to be applied to the G-LED 43*g* in the high-luminance frame.

The respective duty ratios Dr, Db, and Dv of the non-reference colors R, B, and V in the low-luminance frame are each set to the same as the duty ratio Dg of the reference color G in the same low-luminance frame. Therefore, the respective pulse widths of the driving currents to be applied to the R-LED 43*r*, B-LED 43*b*, and V-LED 43*v* in the low-luminance frame are each set to the second pulse width of the driving current to be applied to the G-LED 43*g* in the low-luminance frame.

Note that the setting of the duty ratio D of a non-reference color to the same as the duty ratio D of a reference color is also similar for a case where the DD ratio RD(L/H) is set to less than 1.

Then, the control unit 41 sets a target sensor value SC2(*n*) (i.e., SR(n) for R, SB(n) for B, and SV(n) for V; the same applies hereinafter) for the second color C2 (C2=R, B, V) as a non-reference color.

The target sensor value SC2(n) is calculated in the following manner based on a sensor value SC1(n−2) for the first color C1 (here, the reference color G) in a frame preceding a frame n by two frames (here, sensor value (SG(n−2)) and the color ratio RC(C2/C1) as the internal set value (more specifically, RC(R/G), RC(B/G), and RC(V/G)) (step S22).

$$SC2(n)=SC1(n-2)\times RC(C2/C1).$$

A current value IC2(n) in a current frame is calculated in the following manner from a sensor value SC2(n−2) and a current value IC2(n−2) in a frame preceding the current frame by two frames (note that since the sensor value SC2(n−2) and the current value IC2(n−2) are the values in the frame preceding the current frame by two frames, a sensor value and a current value at the time of previous high-luminance illumination are referred to when high-luminance illumination is then performed, and a sensor value and a current value at the time of previous low-luminance illumination are referred to when low-luminance illumination is then performed (step S23)).

$$IC2(n)=\{IC2(n-2)\times SC2(n)/SC2(n-2)\}$$

Thus, in the frame n, the current value IC2(n) calculated in step S23 and the driving current having the duty ratio D in the non-reference color set in step S21 are applied to the LED in the second color C2 as a non-reference color, and the processing returns to main processing.

Note that the luminance ratio RI(L/H), the DD ratio RD(L/H), and the color ratio RC(C2/C1) are each a fixed value that does not change even when the brightness of the image is changed, as described above. However, it goes without saying that a fixed value to be applied may be made different depending on a configuration of a light source (e.g., a manufacturer or a model number of the LED) or depending on a subject (e.g., depending on whether the subject is a living body or an engine plant or depending on which site of the subject is to be observed even when the subject is a living body).

According to the second embodiment, a substantially similar effect to the effect in the above-described first embodiment is produced, and the target sensor value SC2(n) is calculated based on the sensor value SC1(n−2) in the first color C1 in the frame preceding the current frame by two frames and the color ratio RC(C2/C1). Thus, a highly accurate HDR image can be obtained by synthesizing a high-luminance image and a low-luminance image by maintaining a ratio between respective brightnesses of the luminance images with high accuracy while accurately maintaining a color balance between the first color C1 and the second color C2 and thus, a white balance.

The subject observation system further includes the storage unit 41a configured to store the luminance ratio RI(L/H) and the color ratio RC(C2/C1) in a nonvolatile manner. Thus, when a plurality of fixed values are previously prepared and stored for each of the ratios, the fixed value adapted to an observation target, for example, can be selected, for example, by operating the operation panel 49 so that an HDR image that is easier to observe can be obtained by synthesis.

Further, the pulse widths of the driving currents to be respectively applied to the R-LED 43r, B-LED 43b, and V-LED 43v are each the same as the pulse width of the driving current to be applied to the G-LED 43g in either one of the high-luminance frame and the low-luminance frame. Thus, the white balance can be accurately maintained by simple control.

In addition, if the pulse width of the driving current to be applied to the light source unit in the high-luminance frame and the pulse width of the driving current to be applied to the light source unit in the low-luminance frame are made the same, the control can be made simpler.

Thus, in a subject observation system including a light source apparatus on which light emitting semiconductor devices in a plurality of colors are respectively mounted, shooting of an HDR image using a time divisional method for switching between high-luminance illumination and low-luminance illumination can also be performed while a white balance is maintained.

Note that the above-described processing by the sections may be performed by one or more processors configured as hardware. For example, each of the sections may be a processor configured as an electronic circuit, or may be a circuit section in a processor constituted by an integrated circuit such as an FPGA (field programmable gate array). Alternatively, a processor constituted by one or more CPUs may implement a function as each of sections by reading and executing a processing program recorded on a recording medium.

Although a case where the present invention is the subject observation system has been mainly described above, the present invention may be an operation method for operating the subject observation system as described above, or may be a processing program for causing a computer to perform similar processing to the processing performed by the subject observation system, or a non-transitory computer-readable recording medium storing the processing program, for example.

Further, the present invention is not limited to the above-described embodiments as they are, but may be embodied by modifying components without departing from the gist of the invention in an implementation stage. Various aspects of the invention can be formed by appropriately combining a plurality of components disclosed in the above-described embodiment. Some of all of the components described in the embodiment may be deleted. Further, the components in the different embodiments may be appropriately combined. Accordingly, it goes without saying that various modifications and applications are possible without departing from the scope of the invention.

What is claimed is:

1. A subject observation system comprising:
   a light source configured to generate light having an intensity corresponding to a current value of an applied driving current as illumination light;
   a light sensor configured to detect the intensity of the illumination light to generate a sensor value S;
   an image pickup device configured to pick up an image of return light from a subject irradiated with the illumination light to generate an image pickup signal sequentially for each frame;
   a light source controller configured to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame; and
   a video processor configured to synthesize a high-luminance image pickup signal generated in the high-luminance frame and a low-luminance image pickup signal generated in the low-luminance frame out of the two consecutive high- and low-luminance frames, to generate one high dynamic range image, wherein the light source controller sets, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and applies the driving current to the light source in the n frame such that the target sensor value S(n) is generated by the light sensor.

2. The subject observation system according to claim 1, wherein the light source controller controls the light source such that the intensity of the illumination light in the low-luminance frame takes a value obtained by multiplying the intensity of the illumination light in the high-luminance frame by a luminance ratio RI(L/H) less than 1, and sets, when the (n−1) frame is the high-luminance frame, the target sensor value S(n) to be a value expressed by the following equation 1:

$$S(n)=S(n-1)\times RI(L/H), \text{ and} \qquad \text{[Equation 1]}$$

sets, when the (n−1) frame is the low-luminance frame, the target sensor value S(n) to be a value expressed by the following equation 2:

$$S(n)=S(n-1)/RI(L/H). \qquad \text{[Equation 2]}$$

3. The subject observation system according to claim 2, wherein the light source controller performs control, when a frame preceding the n frame by two frames is an (n−2) frame, a sensor value S generated by the light sensor in the (n−2) frame is S(n−2), a current value of the driving current applied to the light source in the (n−2) frame is I(n−2), and a current value of the driving current applied to the light source in the n frame is I(n), such that the current value I(n) is a value expressed by the following equation 3:

$$I(n)=\{I(n-2)\times S(n)/S(n-2)\}. \qquad \text{[Equation 3]}$$

4. The subject observation system according to claim 3, wherein the light source includes a first light emitting semiconductor device configured to generate light in a first color C1 and a second light emitting semiconductor device configured to generate light in a second color C2 different from the first color C1, and the light sensor includes a first light sensor configured to detect an intensity of the light in the first color C1 to generate a sensor value SC1 as the sensor value S and a second light sensor configured to detect an intensity of the light in the second color C2 to generate a sensor value SC2 as the sensor value S, the light source controller performs control expressed by the equations 1 to 3 for a current value of the driving current applied to the first light emitting semiconductor device by reading the sensor value S as the sensor value SC1, and performs control expressed by the equation 3 for a current value of the driving current applied to the second light emitting semiconductor device by reading the sensor value S as the sensor value SC2, and sets, when a ratio of a light amount of the light in the second color C2 to a light amount of the light in the first color C1 is a color ratio RC(C2/C1), a target sensor value SC2(n) for the second light emitting semiconductor device based on a sensor value SC1(n−2) in the first color C1 in the frame preceding the n frame by two frames and the color ratio RC(C2/C1) using the following equation 4:

$$SC2(n)=SC1(n-2)\times RC(C2/C1). \qquad \text{[Equation 4]}$$

5. The subject observation system according to claim 4, further comprising:

a memory storing the luminance ratio RI(L/H) and the color ratio RC(C2/C1) in a nonvolatile manner, wherein the light source controller performs control by reading out the luminance ratio RI(L/H) and the color ratio RC(C2/C1) from the memory.

6. The subject observation system according to claim 1, wherein the video processor detects a brightness of an image relating to the image pickup signal and generates a light source control signal for setting the brightness to be a target brightness, and the light source controller performs control such that a current value of the driving current applied to the light source in the high-luminance frame becomes constant, and adjusts a first pulse width of the driving current applied to the light source in the high-luminance frame based on the light source control signal and performs control such that a second pulse width of the driving current applied to the light source in the low-luminance frame has a predetermined ratio to the first pulse width.

7. The subject observation system according to claim 4, wherein the video processor detects a brightness of an image relating to the image pickup signal and generates a light source control signal for setting the brightness to be a target brightness, and the light source controller performs control such that a current value of the driving current applied to the light source in the high-luminance frame becomes constant, and adjusts a first pulse width of the driving current applied to the first light emitting semiconductor device in the high-luminance frame based on the light source control signal and performs control such that a second pulse width of the driving current applied to the first light emitting semiconductor device in the low-luminance frame has a predetermined ratio to the first pulse width, and further sets a pulse width of the driving current applied to the second light emitting semiconductor device in the high-luminance frame to the first pulse width and sets a pulse width of the driving current applied to the second light emitting semiconductor device in the low-luminance frame to the second pulse width.

8. The subject observation system according to claim 6, wherein the light source controller further performs control such that the second pulse width is the same as the first pulse width.

9. The subject observation system according to claim 7, wherein the light source controller further performs control such that the second pulse width is the same as the first pulse width.

10. A light source apparatus for an endoscope connectable to an endoscope system comprising an image pickup device configured to pick up an image of return light from a subject irradiated with illumination light to generate an image pickup signal sequentially for each frame and a video processor configured to synthesize, a high-luminance image pickup signal generated in the high-luminance frame and a low-luminance image pickup signal generated in the low-luminance frame out of two consecutive high- and low-luminance frames to generate one high dynamic range image, the light source apparatus for an endoscope comprising:

a light source configured to generate light having an intensity corresponding to a current value of an applied driving current as the illumination light;

a light sensor configured to detect the intensity of the illumination light to generate a sensor value S; and a light source controller configured to apply the driving current to the light source to cause the light source to alternately perform low-luminance illumination in the low-luminance frame and high-luminance illumination in the high-luminance frame and perform control such that an intensity of illumination light in the low-luminance frame has a predetermined luminance ratio to an intensity of illumination light in the high-luminance frame, wherein the light source controller sets, when a temporarily preceding frame and a temporarily succeeding frame out of the two consecutive high- and low-luminance frames are respectively an (n−1) frame and an n frame, and a sensor value S generated by the light sensor in the (n−1) frame is S(n−1), a target sensor value S(n) for the n frame using the sensor value S(n−1) and the luminance ratio, and applies the driving current to the light source in the n frame such that the target sensor value S(n) is generated by the light sensor.

11. A method of operating a subject observation system, the method comprising:

causing a light source to emit light having an intensity corresponding to a current value of an applied driving current as illumination light;

causing a light sensor to detect the intensity of the illumination light to generate a sensor value S;

causing an image pickup device to pick up an image of return light from a subject irradiated with the illumination light sequentially for each frame;

causing a light source controller to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame;

causing a video processor to synthesize a high-luminance image pickup signal generated in the high-luminance frame and a low-luminance image pickup signal generated in the low-luminance frame out of the two consecutive high- and low-luminance frames, to generate one high dynamic range image; and causing the light source controller to set, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and applying the driving current to the light source in the n frame such that the target sensor value S(n) is generated by the light sensor.

12. A non-transitory computer-readable recording medium storing an operation program for a subject observation system executed by a computer, the operation program causing a subject observation system comprising a light source configured to generate illumination light, a light sensor configured to detect an intensity of the illumination light, a light source controller configured to apply a driving current to the light source, an image pickup device configured to pick up an image of return light from a subject irradiated with the illumination light, and a video processor configured to generate an image based on an image pickup signal obtained by image pickup by the image pickup device to:

cause the light source to generate light having an intensity corresponding to a current value of the applied driving current as the illumination light;

cause the light sensor to detect the intensity of the illumination light to generate a sensor value S;

cause the image pickup device to pick up an image of return light from a subject irradiated with the illumination light to generate the image pickup signal sequentially for each frame;

cause the light source controller to apply the driving current to the light source to cause the light source to alternately perform low-luminance illumination in a low-luminance frame and high-luminance illumination in a high-luminance frame and perform control such that an intensity of illumination light in the low-luminance frame has a predetermined luminance ratio to an intensity of illumination light in the high-luminance frame;

cause the video processor to synthesize a high-luminance image pickup signal generated in the high-luminance frame and a low-luminance image pickup signal generated in the low-luminance frame out of the two consecutive high- and low-luminance frames, to generate one high dynamic range image; and cause the light source controller to set, when a temporarily preceding frame and a temporarily succeeding frame out of the high-luminance frame and the low-luminance frame relating to the one high dynamic range image are respectively an (n−1) frame and an n frame, and a sensor value S generated by the light sensor in the (n−1) frame is S(n−1), a target sensor value S(n) for the n frame using the sensor value S(n−1) and the luminance ratio, and apply the driving current to the light source in the n frame such that the target sensor value S(n) is generated by the light sensor.

* * * * *